US00PP27588P2

(12) United States Plant Patent
Barbour

(10) Patent No.: US PP27,588 P2
(45) Date of Patent: Jan. 24, 2017

(54) ***NYSSA* TREE NAMED 'CHERRY PIE'**

(50) Latin Name: *Nyssa sylvatica*
Varietal Denomination: Cherry Pie

(71) Applicant: John Barbour, Hawkinsville, GA (US)

(72) Inventor: John Barbour, Hawkinsville, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 0 days.

(21) Appl. No.: 14/545,864

(22) Filed: Jun. 30, 2015

(51) Int. Cl.
*A01H 5/00* (2006.01)

(52) U.S. Cl.
USPC ..... Plt./216

(58) Field of Classification Search
USPC ..... Plt./216
CPC ..... A01H 5/00
See application file for complete search history.

*Primary Examiner* — Kent L Bell
(74) *Attorney, Agent, or Firm* — C. A. Whealy

(57) ABSTRACT

A new and distinct cultivar of *Nyssa* tree named 'Cherry Pie', characterized by its pyramidal tree form with broad branch angles; vigorous growth habit; freely branching habit with numerous lateral branches providing a full and densely foliated appearance; large glossy medium green-colored leaves that become bright red in color during the autumn; autumn leaf color is uniformly consistent; vaguely ridged and furrowed bark; and production of only male flowers.

5 Drawing Sheets

Botanical designation: *Nyssa sylvatica.*
Cultivar denomination: 'CHERRY PIE'.

BACKGROUND OF THE INVENTION

The present invention relates to a new and distinct cultivar of *Nyssa* tree, botanically known as *Nyssa sylvatica*, commercially referred to as Upland Tupelo or Black Gum and hereinafter referred to by the name 'Cherry Pie'.

The new *Nyssa* tree is a product of a planned breeding program conducted by the Inventor in Hillsboro County, Ga. and Franklin County, Tenn. The objective of the breeding program is to create new *Nyssa* trees appropriate for urban landscapes that have an upright pyramidal tree form, vigorous growth habit and uniformly consistent bright red autumn leaf color.

The new *Nyssa* tree originated from an open-pollination of an unnamed selection of *Nyssa sylvatica*, not patented, as the female, or seed, parent with an unknown selection of *Nyssa sylvatica* as the male, or pollen, parent. The new *Nyssa* tree was discovered and selected by the Inventor as a single plant from within the progeny of the stated open-pollination in a controlled environment in Pulaski County, Ga. in October, 2006.

Asexual reproduction of the new *Nyssa* tree by chip budding in a controlled environment in Franklin County, Tenn. has shown that the unique features of this new *Nyssa* tree are stable and reproduced true to type in successive generations.

SUMMARY OF THE INVENTION

Trees of the new *Nyssa* have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Cherry Pie'. These characteristics in combination distinguish 'Cherry Pie' as a new and distinct *Nyssa* tree:

1. Pyramidal tree form with broad branch angles.
2. Vigorous growth habit.
3. Freely branching habit with numerous lateral branches providing a full and densely foliated appearance.
4. Large glossy medium green-colored leaves that become bright red in color during the autumn; autumn leaf color is uniformly consistent.
5. Vaguely ridged and furrowed bark.
6. Male flowers are only present on trees of the new *Nyssa.*

Trees of the new *Nyssa* can be compared to trees of the female parent selection. Trees of the new *Nyssa* differ primarily from trees of the female parent selection in the following characteristics:

1. Trees of the new *Nyssa* exhibit bright red-colored leaves in the autumn whereas trees of the female parent selection do not exhibit red-colored leaves in the autumn.
2. Trees of the new *Nyssa* only produce male flower whereas trees of the female parent selection only produce female flowers.

Trees of the new *Nyssa* can also be compared to trees of *Nyssa sylvatica* 'NSUHH', disclosed in U.S. Plant Pat. No. 22,951. Trees of the new *Nyssa* and 'NSUHH' differ primarily in the following characteristics:

1. Trees of the new *Nyssa* have broad branch angles and are pyramidal in form whereas trees of 'NSUHH' have narrow branch angles and are upswept pyramidal (gable) in form.
2. Trees of the new *Nyssa* are more vigorous than trees of 'NSUHH'.
3. Trees of the new *Nyssa* are more freely branching than trees of 'NSUHH'.

4. Leaves of trees of the new *Nyssa* are longer and broader than leaves of trees of 'NSUHH'.
5. During the summer, leaves of trees of the new *Nyssa* are lighter green in color than leaves of trees of 'NSUHH'.
6. During the autumn, leaves of trees of the new *Nyssa* are brighter red in color than leaves of trees of 'NSUHH'; in addition, trees of the new *Nyssa* are more uniformly red in color than plants of 'NSUHH' which exhibit both red and green-colored leaves during the autumn.
7. Trees of the new *Nyssa* and 'NSUHH' differ in bark texture as trees of the new *Nyssa* have vaguely ridged and furrowed bark whereas trees of 'NSUHH' have smooth and fissured bark.
8. Trees of the new *Nyssa* flower about two to three weeks earlier than trees of 'NSUHH'.

BRIEF DESCRIPTION OF THE PHOTOGRAPHS

The accompanying colored photographs illustrate the overall appearance of the new *Nyssa* tree showing the colors as true as it is reasonably possible to obtain in colored reproductions of this type. Colors in the photographs may differ slightly from the color values cited in the detailed botanical description which accurately describe the colors of the new *Nyssa* tree.

The photograph on the first sheet is a side perspective view of a typical ten-year old tree of 'Cherry Pie' grown during the summer in an outdoor nursery.

The photographs on the second sheet are side perspective views of typical six-year old trees of 'Cherry Pie'(left) and 'NSUHH' (right) grown during the winter in an outdoor nursery showing the differences in branch angle orientation and overall tree form.

The photographs on the third sheet are side perspective views of typical six-year old trees of 'Cherry Pie' (left) and 'NSUHH' (right) grown during the autumn in an outdoor nursery showing the differences in leaf color and uniformity of autumn leaf color.

The photograph on the fourth sheet is a close-up view of the upper surfaces of typical leaves of 'Cherry Pie' (upper left) and 'NSUHH' (bottom right) grown during the summer in an outdoor nursery showing the differences in leaf size, shape and color.

The photographs on the fifth sheet are close-up views of the trunk of typical six-year old trees of 'Cherry Pie' (left) and 'NSUHH' (right) grown during the winter in an outdoor nursery showing the differences in bark texture.

DETAILED BOTANICAL DESCRIPTION

The aforementioned photographs and following observations, measurements and values describe trees grown in an outdoor nursery in Pulaski County, Ga. and under cultural practices typical of commercial *Nyssa* tree production. Trees used in the photographs were six and ten years old. Trees used for the following description were six years old. During the production of the trees, average day temperature was 24.5° C. and average night temperature was 11.1° C. In the following description, color references are made to The Royal Horticultural Society Colour Chart, 2007 Edition, except where general terms of ordinary dictionary significance are used.

Botanical classification: *Nyssa sylvatica* 'Cherry Pie'.

Parentage:

*Female, or seed, parent*.—Unnamed selection of *Nyssa sylvatica*, not patented.

*Male, or pollen, parent*.—Unknown selection of *Nyssa sylvatica*, not patented.

Propagation:

*Type*.—By chip budding the new *Nyssa* tree onto an unnamed selection of *Nyssa sylvatica* understock.

Tree description:

*Tree form and growth habit*.—Deciduous tree with broad branching habit and pyramidal tree form; freely branching habit with about 70 lateral branches developing per tree; full and densely-foliated appearance; vigorous growth habit; dioecious, only male flower initiation and development have been observed on trees of the new *Nyssa*.

*Tree height*.—About 5.03 meters.

*Tree width* (*spread*).—About 2.44 meters.

*Trunk caliper*.—About 10.8 cm.

*Growth rate, height*.—About 84 cm per year.

*Growth rate, caliper*.—About 1.8 cm per year.

*Branch angle orientation*.—Mid-tree canopy branches, about 62° from vertical.

*Internode length*.—About 3.2 cm on one-year old wood.

*Lateral branch color*.—Light reddish brown.

*Immature bark texture*.—Smooth, glabrous.

*Mature bark texture*.—Woody; vaguely ridged and furrowed.

*Mature bark color*.—Close to N200C; inner exfoliated bark, close to 156B to 156C.

Leaf description:

*Arrangement*.—Alternate, simple.

*Length*.—About 14.08 cm.

*Width*.—About 5.34 cm.

*Shape*.—Ovate.

*Apex*.—Acuminate.

*Base*.—Cuneate to acute.

*Margins*.—Entire.

*Venation pattern*.—Pinnate.

*Texture, upper and lower surfaces*.—Smooth, glabrous; young leaves, pubescent.

*Luster, upper surface*.—Glossy.

*Luster, lower surface*.—Somewhat glossy.

*Color*.—When developing, upper surface: Close to 144B. When developing, lower surface: Close to 149D. Fully developed, upper surface: Close to 137A to 137B; in the autumn, close to 44A, 45A and 46A; venation, close to 146C. Fully developed, lower surface: Close to 146B; in the autumn, close to 50C to 50D; venation, close to 146D.

*Petioles*.—Length: About 1.6 cm. Diameter: About 2.9 mm. Texture, upper and lower surfaces: Smooth, glabrous. Color, upper surface: Close to 144A. Color, lower surface: Close to 144B.

Flower description:

*Flower arrangement and habit*.—Dioecious; only male flowers have been observed to develop; flowers simple and inconspicuous; flowers arranged in oval to rounded racemes with usually about ten to twelve flowers per raceme.

*Fragrance*.—None detected.

*Natural flowering season*.—Trees of the new *Nyssa* begin flowering in early to mid-April in Pulaski County, Ga.

*Flower longevity*.—Individual flowers last about ten days to two weeks on the tree; flowers not persistent.

*Inflorescence height*.—About 2 cm.

*Inflorescence diameter*.—About 1.7 cm.

*Flower diameter*.—About 6 mm.

*Flower length* (*depth*).—About 3.5 mm.

*Terminal flower buds*.—Length: About 5.9 mm. Diameter: About 4.1 mm. Texture: Smooth, glabrous. Color: Close to 200A.

*Lateral flower buds*.—Length: About 4.4 mm. Diameter: About 2.9 mm. Texture: Smooth, glabrous. Color: Close to 200A.

*Petals*.—None observed.

*Sepals*.—Quantity and arrangement: About eight sepals arranged in a single whorl. Length: About 1 mm. Width: About 0.5 mm. Shape: Ovate. Apex: Acute; reflexing. Margin: Entire. Texture, upper and lower surfaces: Smooth, glabrous. Color: When opening, upper and lower surfaces: Close to 145A. Fully opened, upper and lower surfaces: Close to 145A.

*Peduncles*.—Length: About 1.6 cm. Diameter: About 1.3 mm. Strength: Strong, flexible. Texture: Slightly pubescent. Color: Close to 144B to 144C.

*Pedicels*.—Length: About 5 mm. Diameter: About 0.5 mm. Strength: Strong, flexible. Texture: Smooth, glabrous. Color: Close to 144B to 144C.

*Reproductive organs*.—Stamens: Quantity: About eight to ten per flower. Filament length: About 2 mm to 4 mm. Filament color: Close to 154A to 154B. Anther length: About 1 mm. Anther diameter: About 1 mm. Anther color: Close to 154B to 154C. Pollen amount: About 32 grains per 1 $mm^2$. Pollen color: Close to 2C. Pistils: None observed, male flowers only observed. Seeds and fruits: None observed, male flowers only observed.

Temperature tolerance: Trees of the new *Nyssa* have been observed to tolerate high temperatures about 40.5° C. and low temperatures about −18.9° C. when grown in USDA Hardiness Zone 6.

Pathogen & pest resistance: Trees of the new *Nyssa* have been not observed to be resistant to pathogens and pests common to *Nyssa* trees.

It is claimed:

1. A new and distinct *Nyssa* tree named 'Cherry Pie' as illustrated and described.

* * * * *

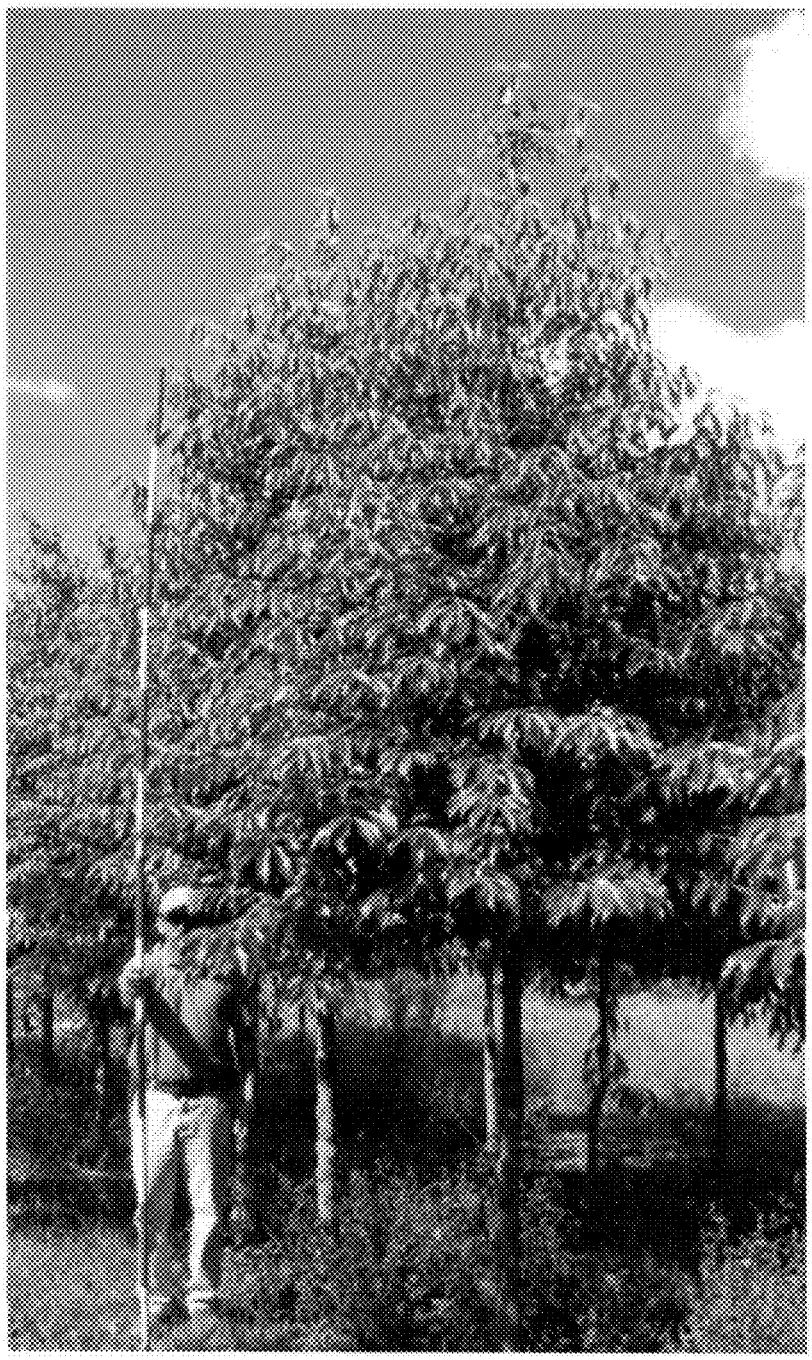

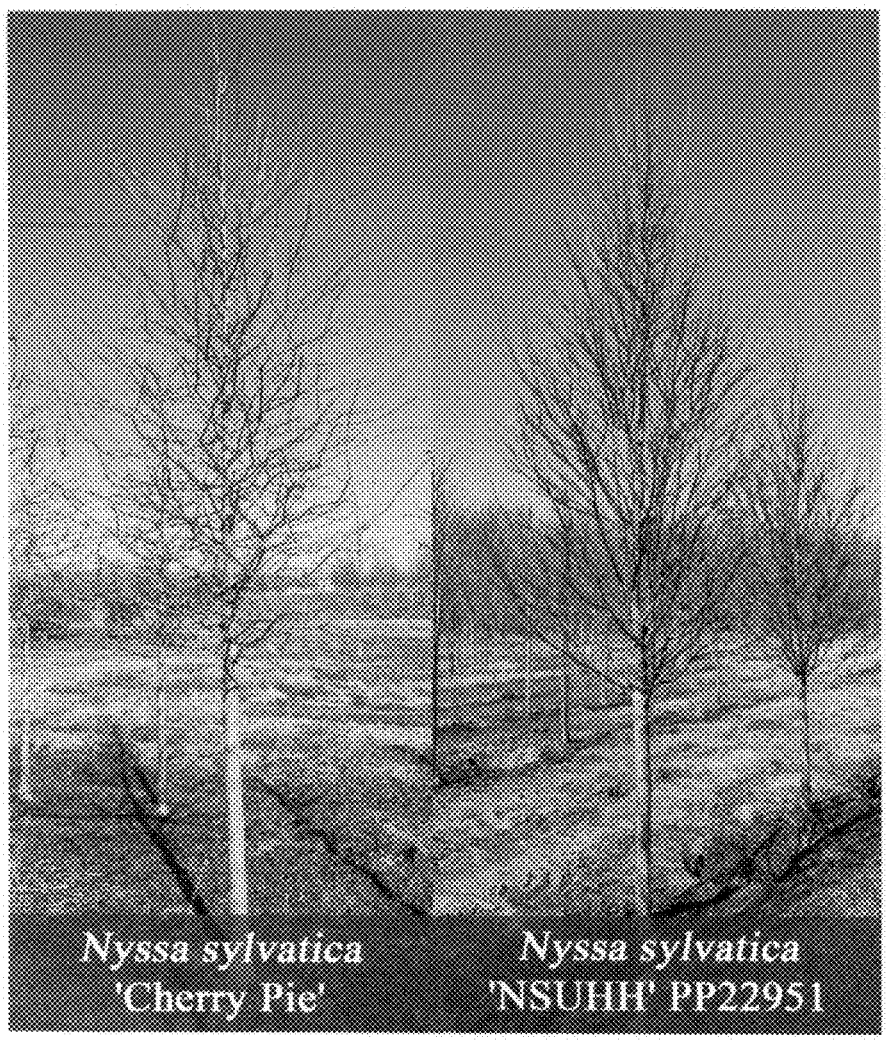
*Nyssa sylvatica*
'Cherry Pie'
*Nyssa sylvatica*
'NSUHH' PP22951

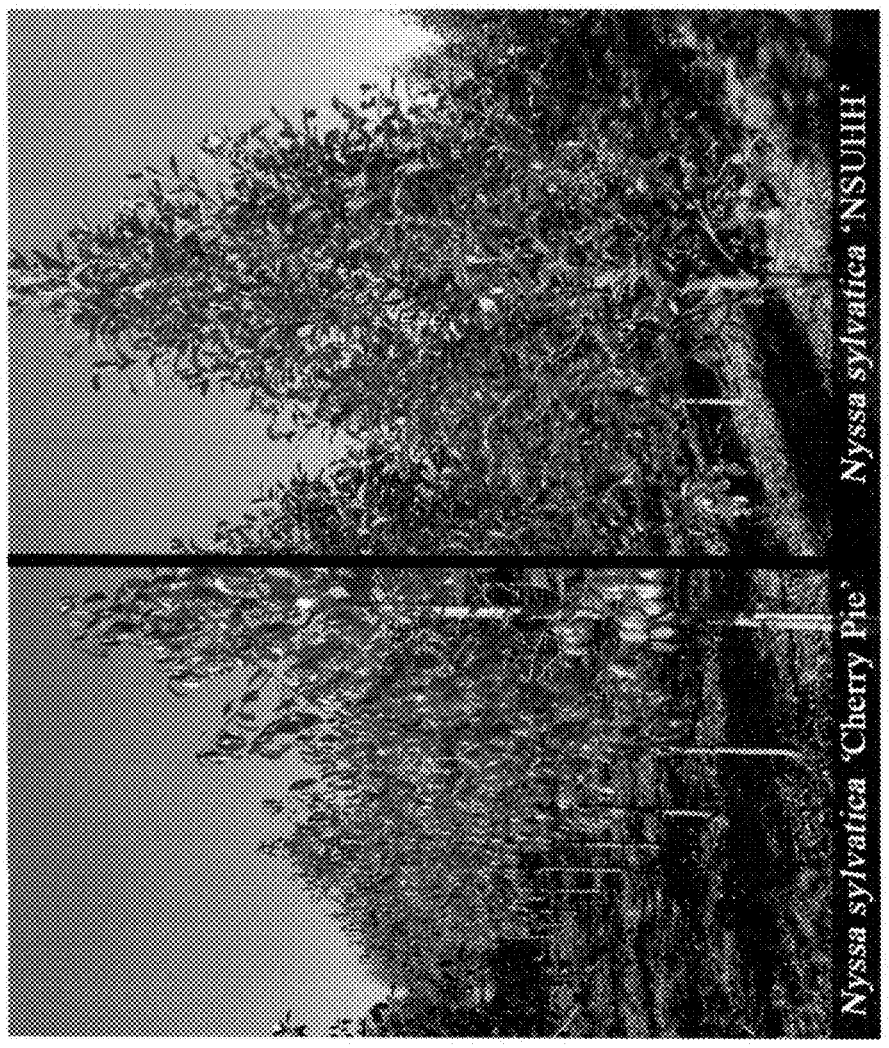
*Nyssa sylvatica* 'Cherry Pie'
*Nyssa sylvatica* 'NSUHH'

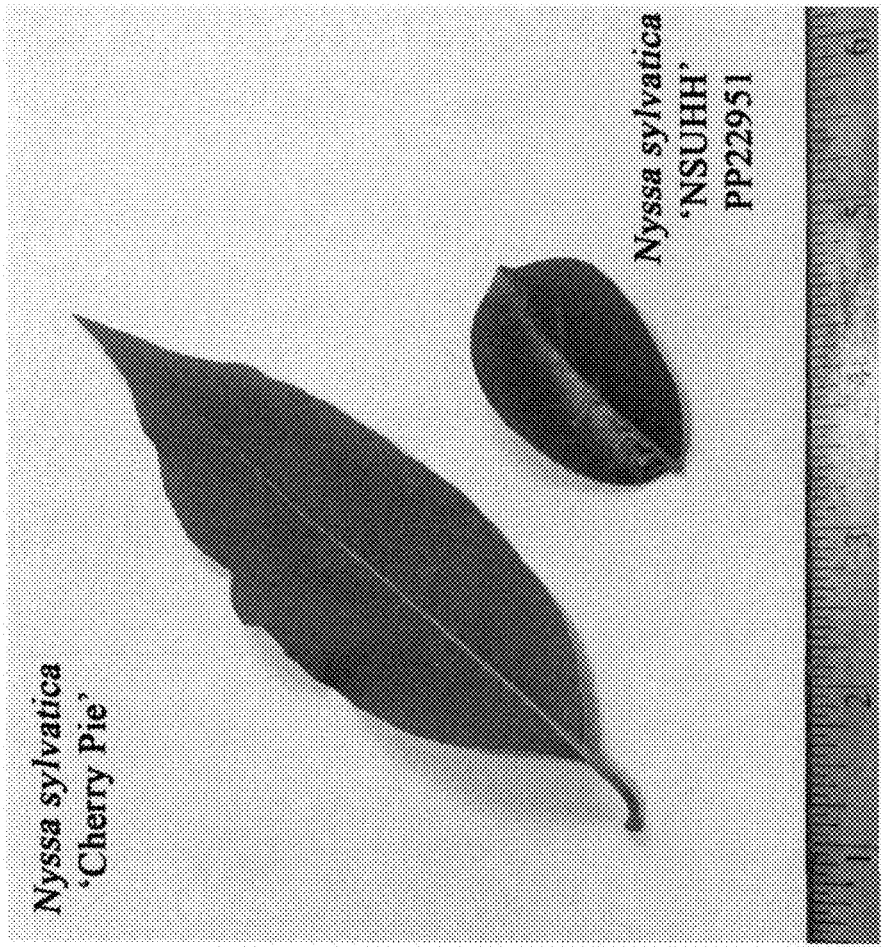
Nyssa sylvatica
'Cherry Pie'
Nyssa sylvatica
'NSUHH'
PP22951

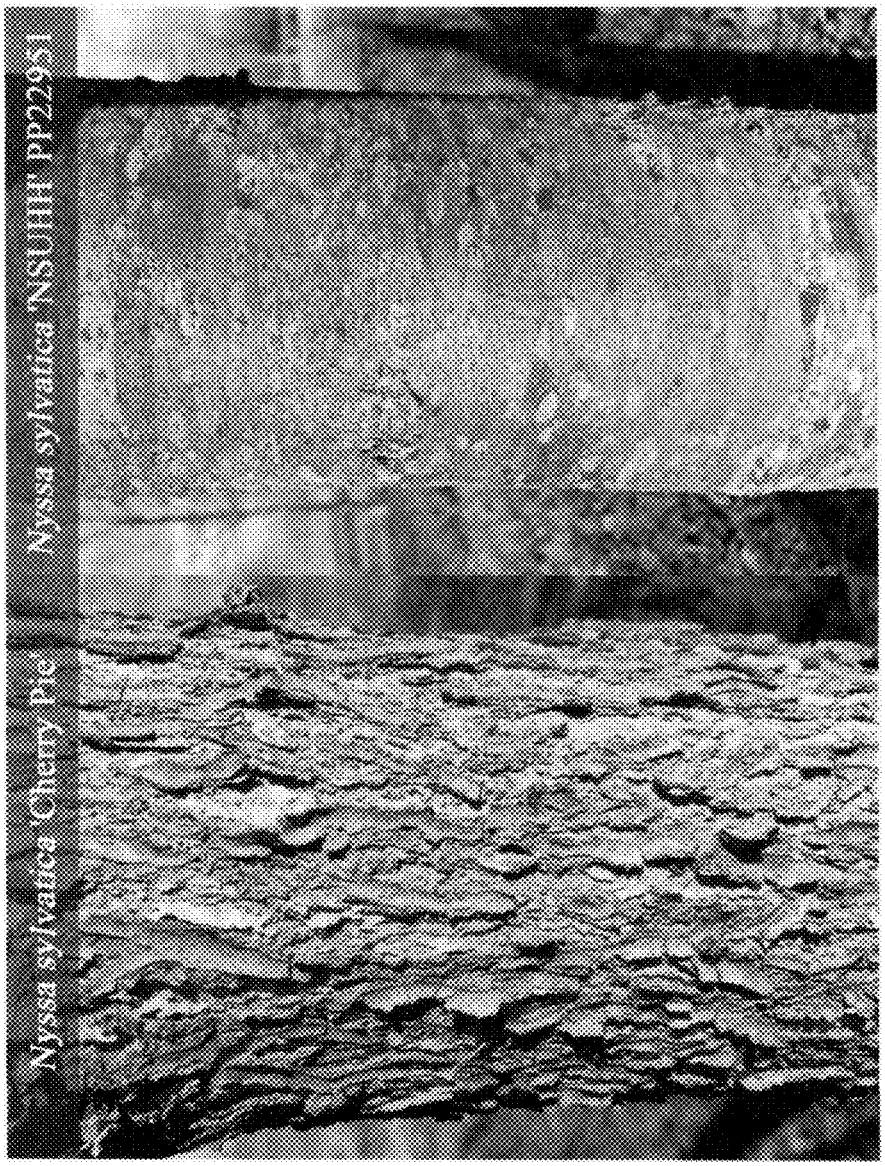
Nyssa sylvatica 'Cherry Pie'
Nyssa sylvatica 'NSUHH' PP27,581